(12) United States Patent
Okamoto et al.

(10) Patent No.: US 8,895,244 B2
(45) Date of Patent: Nov. 25, 2014

(54) METHOD AND KIT FOR DETECTING 5-HYDROXYMETHYLCYTOSINE IN NUCLEIC ACIDS

(75) Inventors: Akimitsu Okamoto, Wako (JP); Kaori Sugizaki, Wako (JP); Akiko Nakamura, Wako (JP); Hiroyuki Yanagisawa, Wako (JP); Shuji Ikeda, Wako (JP)

(73) Assignee: Riken, Wako-shi, Saitama (JP)

( * ) Notice: Subject to any disclaimer, the term of this patent is extended or adjusted under 35 U.S.C. 154(b) by 0 days.

(21) Appl. No.: 14/111,825

(22) PCT Filed: Apr. 16, 2012

(86) PCT No.: PCT/JP2012/060265
§ 371 (c)(1),
(2), (4) Date: Oct. 15, 2013

(87) PCT Pub. No.: WO2012/141324
PCT Pub. Date: Oct. 18, 2012

(65) Prior Publication Data
US 2014/0045183 A1 Feb. 13, 2014

(30) Foreign Application Priority Data

Apr. 15, 2011 (JP) ................................ 2011-090971

(51) Int. Cl.
*C12Q 1/68* (2006.01)
*B01L 3/00* (2006.01)

(52) U.S. Cl.
USPC ........................................... 435/6.1; 422/430

(58) Field of Classification Search
USPC .......................................... 435/6.1; 422/430
See application file for complete search history.

(56) References Cited

FOREIGN PATENT DOCUMENTS

WO WO 2006/132022 A1 12/2006
WO WO 2007/111324 A1 10/2007

OTHER PUBLICATIONS

International Search Report (PCT/ISA/210) mailed on May 22, 2012, by the Japanese Patent Office as the International Searching Authority for International Application No. PCT/JP2012/060265.
Written Opinion (PCT/ISA/237) mailed on May 22, 2012, by the Japanese Patent Office as the International Searching Authority for International Application No. PCT/JP2012/060265.
Tahiliani M et al., Conversion of 5-methylcytosine to 5-hydroxymethylcytosine in mammalian DNA by MLL partner TET1., Science, May 15, 2009, vol. 324, No. 5929, pp. 930-935.
Ito S et al., Role of Tet proteins in 5mC to 5hmC conversion, ES-cell self-renewal and inner cell mass specification, Nature, Aug. 26, 2010, vol. 466, No. 7310, pp. 1129-1133.

(Continued)

*Primary Examiner* — Jezia Riley
(74) *Attorney, Agent, or Firm* — Buchanan, Ingersoll & Rooney PC (57) ABSTRACT

Provided are a method and a kit for detecting 5-hydroxymethylcytosine in a nucleic acid. The method is a method for detecting 5-hydroxymethylcytosine in a nucleic acid, comprising the steps of: (1) oxidizing 5-hydroxymethylcytosine in a nucleic acid sample by treating the nucleic acid sample with a tungstic acid-based oxidizing agent comprising peroxotungstic acid, tungstic acid, a salt thereof, or a combination thereof with a reoxidizing agent; and (2) determining the position of the oxidized 5-hydroxymethylcytosine in the nucleic acid sample.

8 Claims, 4 Drawing Sheets

(56) References Cited

OTHER PUBLICATIONS

Munzel M et al., Quantification of the Sixth DNA Base Hydroxymethylcytosine in the Brain, Angew. Chem. Int. Ed., vol. 49, No. 31, Jul. 19, 2010, pp. 5375-5377.

Song CX et al., Selective chemical labeling reveals the genome-wide distribution of 5-hydroxymethylcytosine, [online] Nat. Biotechnol., vol. 29, No. 1, Dec. 12, 2010, pp. 68-72.

Kamata K et al., Hydrogen-bond-assisted epoxidation of homoallylic and allylic alcohols with hydrogen peroxide catalyzed by selenium-containing dinuclear peroxotungstate., J. Am. Chem. Soc., May 27, 2009, vol. 131, No. 20, pp. 6997-7004.

Okamoto A et al., 5-Hydroxymethylcytosine-selective oxidation with peroxotungstate., Chem. Commun., vol. 47, No. 40, Oct. 28, 2011, pp. 11231-11233.

Elucidation of Initialization of Celluar Function Using Tungsten Oxidizer, "Japan Science and Technology Agency" Aug. 30, 2011.

FIG. 1

TARGET MOLECULAR STRUCTURE
5-HYDROXYMETHYLCYTOSINE

● represents DNA, RNA, nucleotide, nucleoside, nucleic acid analog, peptide, organic polymer.

METHOD AND KIT FOR DETECTING 5-HYDROXYMETHYLCYTOSINE IN NUCLEIC ACIDS

TECHNICAL FIELD

The present invention relates to a method and a kit for detecting 5-hydroxymethylcytosine in a nucleic acid.

BACKGROUND ART

Epigenetics includes DNA methylation in which a genome is physiologically modified and posttranslational modification of chromatin which is a complex of DNA and proteins and a large number of proteins constituting chromatin, which integrally control the gene expression.

Regarding modification of histones in chromatin, structural alteration of chromatin by histone modification plays an important role in the induction of transcription. For example, acetylation by a histone acetylation enzyme triggers the induction of remodeling of chromatin, so that transcription is started by general transcription factors and a RNA polymerase. In addition, methylation or phosphorylation of histones controls the transcription and causes silencing, chromatin condensation, and the like.

In addition, in the genomes of many eukaryotes, 60 to 90% of CpG dinucleotides are methylated at the 5-carbon atom position of cytosine. The methylated CpG is found in heterochromatins and transposons containing many repeated sequences, and thought to suppress the activation of viruses and transposons. In addition, the CpG methylation and the histone modification coordinate with each other.

An exception is that CG-rich regions (CpG islands) present in promoter regions of many genes are not methylated. In addition, an exception to the exception is that CpG islands are methylated in genes to be imprinted and in the inactive X chromosome of females. In addition, CpG islands are methylated also in the promoter regions of tumor suppressor gene in cancer cells. Hence, methylation of cytosine can be used as a marker of development, recurrence, and metastasis of cancer. In this respect, a simple method for detecting whether or not cytosine in a gene is methylated has been sought.

As described above, 5-methylcytosine, which is a methylated cytosine (C), has been reported to be present in the DNA, and has been known to play an important role in the developmental genetics, so far. Recently, a new base (5-hydroxymethylcytosine) has been discovered in a study of Purkinje cells (Non Patent Literature 1). It is pointed out that 5-hydroxymethylcytosine is a key for elucidating the mechanism of DNA demethylation (reprogramming). Hence, specifying the presence and the position of 5-hydroxymethylcytosine in a DNA is important and essential as a core technology for investigating the reprogramming of a gene function in all the fields associated with epigenetics technologies, such as the fields of cancer, aging, and regenerative medicine.

Various methods have been proposed for chemically and easily detecting methylcytosine in a DNA. Patent Document 1 describes a method for distinguishing cytosine from methylcytosine. In addition, Patent Document 2 describes a method in which a target DNA is selectively cleaved at the position of 5-methylcytosine to obtain a 5'-fragment, an enzymatic reaction is carried out by using a FRET probe capable of hybridizing with the 5'-fragment and a flap endonuclease, and then the fluorescence is detected.

However, none of these methods can be applied directly to the detection of 5-hydroxymethylcytosine.

Known methods for detecting 5-hydroxymethylcytosine in a DNA include a method in which 5-hydroxymethylcytosine in a fragmented DNA sample is detected by applying the conventional immunoprecipitation method using an anti-5-hydroxymethylcytosine antibody (Non Patent Literatures 2 and 3), a method in which 5-hydroxymethylcytosine is modified with a sugar by using an enzyme capable of the sugar modification, and the modified 5-hydroxymethylcytosine is isolated (Non Patent Literature 4), and the like.

However, each of the method requires that a DNA sample be fragmented in advance, and has a problem that even when a fragment containing 5-hydroxymethylcytosine is isolated, the position of the 5-hydroxymethylcytosine in the fragment cannot be specified.

Hence, there is a demand for a method for chemically and easily detecting 5-hydroxymethylcytosine in a nucleic acid such as a DNA.

CITATION LIST

Patent Literatures

Patent Literature 1: WO2006/132022
Patent Literature 2: WO2007/111324
Non Patent Literatures
Non Patent Literature 1: Science Vol. 324, No. 5929, pp. 930-935 (2009)
Non Patent Literature 2: Nature 466, 1129-1133 (2010)
Non Patent Literature 3: Angew. Chem. Int. Ed. 49, 5375-5377 (2010)
Non Patent Literature 4: Nature Biotechnol. 29, 68-72 (2011)

SUMMARY OF INVENTION

Technical Problems

An object of the present invention is to provide a method for detecting 5-hydroxymethylcytosine in a nucleic acid.

Another object of the present invention is to provide a kit for detecting 5-hydroxymethylcytosine in a nucleic acid.

Solution to Problems

The present invention provides the following method and kit for detecting 5-hydroxymethylcytosine in a nucleic acid.
1. A method for detecting 5-hydroxymethylcytosine in a nucleic acid, comprising the steps of:
    (1) oxidizing 5-hydroxymethylcytosine possibly present in a nucleic acid sample by treating the nucleic acid sample with a tungstic acid-based oxidizing agent; and
    (2) determining the position of the oxidized 5-hydroxymethylcytosine in the nucleic acid sample.
2. The method according to 1, wherein
    the tungstic acid-based oxidizing agent is at least one selected from the group consisting of
    (1) peroxotungstic acid, or a salt thereof,
    (2) tungstic acid, or a salt thereof, and
    (3) combinations of peroxotungstic acid, tungstic acid, or a salt thereof with a reoxidizing agent.
3. The method according to 1, wherein
    the tungstic acid-based oxidizing agent is at least one selected from the group consisting of $K_2[\{W(=O)(O_2)_2(H_2O)\}_2(\beta-O)]$, $H_2WO_4/H_2O_2$, and $K_2WO_4/H_2O_2$.
4. The method according to any one of 1 to 3, wherein
    the step (2) comprises a step of determining the position of the oxidized 5-hydroxymethylcytosine by cleaving the oxidized nucleic acid sample at the position of the oxidized 5-hydroxymethylcytosine by a deamination treatment, and measuring the size of a fragment of the nucleic acid.

5. The method according to any one of 1 to 3, wherein the step (2) comprises a step of determining the position of the oxidized 5-hydroxymethylcytosine by sequencing the oxidized nucleic acid sample.

6. The method according to any one of 1 to 5, wherein the nucleic acid is a DNA.

7. Use of at least one tungstic acid-based oxidizing agent for detecting 5-hydroxymethylcytosine in a nucleic acid, the at least one tungstic acid-based oxidizing agent being selected from the group consisting of
   (1) peroxotungstic acid, or a salt thereof,
   (2) tungstic acid, or a salt thereof, and
   (3) combinations of peroxotungstic acid, tungstic acid, or a salt thereof with a reoxidizing agent.

8. A kit for detecting 5-hydroxymethylcytosine in a nucleic acid, comprising at least one tungstic acid-based oxidizing agent selected from the group consisting of
   (1) peroxotungstic acid, or a salt thereof,
   (2) tungstic acid, or a salt thereof, and
   (3) combinations of peroxotungstic acid, tungstic acid, or a salt thereof with a reoxidizing agent.

9. The kit according to 8, further comprising at least one selected from the group consisting of reagents for a deamination treatment of an oxidized nucleic acid sample, and pH buffer solutions.

Advantageous Effects of Invention

The present invention makes it possible to chemically, easily, and accurately detect the presence and the position of 5-hydroxymethylcytosine in a nucleic acid. Hence, the present invention is extremely useful as a core technology for investigating the reprogramming of a gene function in all the fields associated with epigenetics technologies, such as the fields of cancer, aging, and regenerative medicine.

BRIEF DESCRIPTION OF DRAWINGS

Parts (A) to (F) of FIG. 5 are images of polyacrylamide gel electrophoresis of products obtained in Example 3 from DNAs of SEQ ID NOs: 4 to 9 by an oxidation treatment with $K_2[\{W(=O)(O_2)_2(H_2O)\}_2(\mu\text{-}O)]$ and a subsequent piperidine treatment.

Parts (G) to (K) of FIG. 6 are images of polyacrylamide gel electrophoresis of products obtained in Example 3 from DNAs of SEQ ID NOs: 10 to 14 by an oxidation treatment with $K_2[\{W(=O)(O_2)_2(H_2O)\}_2(\mu\text{-}O)]$ and a subsequent piperidine treatment.

DESCRIPTION OF EMBODIMENTS

Figure 1:
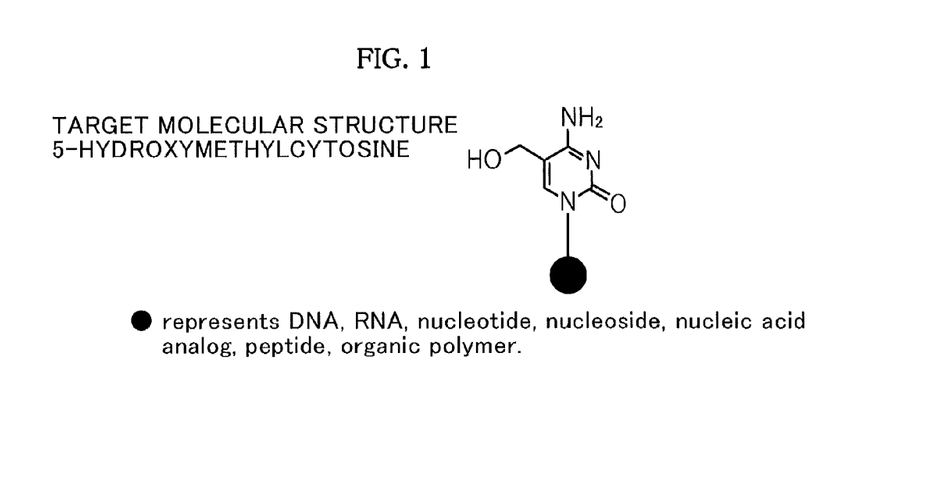
FIG. 1 is a diagram illustrating an example of a nucleic acid preferable as a target of the method of the present invention.

In the present invention, the "nucleic acid" means any compound which contains 5-hydroxymethylcytosine as a part of its structure as shown in FIG. 1, and whose 5-hydroxymethylcytosine can be detected by the method of the present invention. The meaning of "Nucleic acid" include DNAs, RNAs, nucleotides, nucleosides, nucleic acid analogs, peptides, other organic polymers, and the like. DNAs are particularly preferable. The method of the present invention can be applied to a nucleic acid having any chain length, and the chain length is preferably 1 to 10000 bp, and further preferably 15 to 1000 bp.

The "tungstic acid-based oxidizing agent" used in the present invention is an oxidizing agent capable of selectively acting on and oxidizing 5-hydroxymethylcytosine in a nucleic acid. The "tungstic acid-based oxidizing agent" is preferably at least one selected from the group consisting of (1) peroxotungstic acid, or a salt thereof (for example, alkali metal salts such as potassium salts and sodium salts; ammonium salts; amine salts; and the like), (2) tungstic acid, or a salt thereof (for example, alkali metal salts such as potassium salts and sodium salts; ammonium salts; amine salts; and the like), and (3) combinations of peroxotungstic acid, tungstic acid, or a salt thereof with a reoxidizing agent.

As the oxidizing agent of the present invention, peroxotungstic acid, tungstic acid, or a salt thereof may be used alone or in combination with a reoxidizing agent.

Specific examples of the peroxotungstic acid, tungstic acid, or a salt thereof include $K_2[\{W(=O)(O_2)_2(H_2O)\}_2(\mu\text{-}O)]$, $H_2WO_4$, $K_2WO_4$, $Na_2WO_4$—$NH_2CH_2PO_3H_2$—$[CH_3(n\text{-}C_8H_{17})_3N]HSO_4$, $[C_5H_5N(n\text{-}C_{16}H_{33})]_3PW_{12}O_{40}$, $[(n\text{-}C_4H_9)_4N]_2[PhPO_3\{WO(O_2)_2\}]$, salts of $\{WZn[M(H_2O)]_2(ZnW_9O_{34})_2\}$ (where M represents Zn, Mn, Ru, Fe, or the like), $Na_2WO_4$-fructopyranoside, and the like.

Specific examples of the reoxidizing agent include hydrogen peroxide, N-methylmorpholine-N-oxide, potassium ferricyanide, peroxybenzoic acid, oxygen gas, and the like.

When a combination with a reoxidizing agent is employed, the molar ratio (peroxotungstic acid, tungstic acid, or a salt thereof/reoxidizing agent) of the peroxotungstic acid, tungstic acid, or salt thereof to the reoxidizing agent is preferably 1/100000 to 1/1, further preferably 1/100 to 1/1, and generally 1/10.

Oxidation Treatment Step of Nucleic Acid

In the present invention, 5-hydroxymethylcytosine present in the nucleic acid can be selectively oxidized by bringing the oxidizing agent of the present invention into contact with a nucleic acid-containing sample.

In the oxidation reaction, only 5-hydroxymethylcytosine is selectively oxidized, whereas neither cytosine nor 5-methylcytosine is oxidized. Hence, only 5-hydroxymethylcytosine can be selectively detected.

In this oxidation reaction, the pH of an aqueous solution of the nucleic acid sample is not particularly limited, and is desirably adjusted to preferably pH 1 to 10, and further preferably pH 5 to 9 with an appropriate buffer solution of, for example, sodium phosphate, Tris-hydrochloric acid, sodium acetate, or the like.

In addition, the concentration of the nucleic acid sample is not particularly limited, and is preferably $10^{-7}$ to 10% by mass, and further preferably $10^{-5}$ to $10^{-1}$ % by mass.

The amount of the oxidizing agent of the present invention added is not particularly limited, and is preferably 0.1 to $10^6$ parts by mass, and further preferably $10^2$ to $10^5$ parts by mass relative to 100 parts by mass of the nucleic acid sample.

The reaction time of the oxidation reaction is preferably 1 minute to 48 hours, and further preferably 10 minutes to 10 hours, and the temperature of the oxidation reaction is preferably 0 to 100° C., and further preferably 5 to 70° C.

Step of Determining Position of 5-Hydroxymethylcytosine in Oxidized Nucleic Acid After the oxidation reaction, the position of 5-hydroxymethylcytosine is determined.

Here, if there is a possibility that the residue of the reaction reagent may cause problems, such as amplification failure, in the subsequent detection step, a desalination operation is carried out before the detection step. The desalination operation can be carried out by a known method such as gel filtration, gel electrophoresis, HPLC purification, a method using a desalination filter, a method using an ion exchange column, salting-out, or the like. This desalination treatment can improve the precision of the subsequent step of determining the position of 5-hydroxymethylcytosine.

The method for determining the position of 5-hydroxymethylcytosine in the oxidized nucleic acid is not particularly limited, and examples thereof include the following methods:

(A) a method in which the position of the oxidized 5-hydroxymethylcytosine is determined by cleaving the oxidized nucleic acid sample at the position of the oxidized 5-hydroxymethylcytosine by a deamination treatment, and measuring the size of a fragment of the nucleic acid; and (B) a method in which the position of the oxidized 5-hydroxymethylcytosine is determined by sequencing the oxidized nucleic acid sample.

First, the method (A) is described.

The 5-hydroxymethylcytosine subjected to the oxidation treatment is treated under reaction conditions for inducing deamination of the cytosine 4 position (for example, heating in a buffer solution of pH 4 to 9, heating in an aqueous solution containing a salt such as lithium bromide or magnesium bromide, heating in an aqueous solution containing a basic substance such as sodium hydroxide or piperidine, or the like). Thus, the nucleic acid is cleaved at the position of the oxidized 5-hydroxymethylcytosine. Then, the size of a fragment of the nucleic acid is determined based on the electrophoretic mobility determined by electrophoresis (using polyacrylamide gel, agarose gel, or the like) or based on the change in mass determined by mass spectrometry (MALDI, ESI, or the like). For the determination of the size of the fragment of the nucleic acid based on the electrophoretic mobility determined by electrophoresis or the like, the nucleic acid sample is desirably labeled with a fluorescent substance, $^{32}P$-phosphoric acid, digoxigenin, or the like in advance.

More specifically, the nucleic acid sample subjected to the oxidation treatment is subjected to a heat treatment (preferably at 70 to 100° C. and preferably for 5 minutes to 5 hours) in an aqueous solution containing a basic substance such as piperidine or sodium hydroxide (the concentration is preferably about 3 to 50% by mass, and further preferably about 10 to 20% by mass). As a consequence, the N-glycosidic bond between the oxidized 5-hydroxymethylcytosine base and the sugar is cleaved, and phosphodiester bonds between the nucleotide having the oxidized 5-hydroxymethylcytosine and adjacent nucleotides are also cleaved. Hence, the position of the base of interest can be specified by, after the treatment with a basic substance, amplifying a fragment of the nucleic acid by PCR or the like, and measuring the size of the fragment of the nucleic acid by, for example, polyacrylamide gel electrophoresis or the like. In other words, since the nucleic acid is cleaved at the position where the 5-hydroxymethylcytosine is present, and a band of a fragment of the nucleic acid can be observed, the position of 5-hydroxymethylcytosine in the sequence can be determined.

Next, the method (B) is described.

A sequencing reaction (using an ordinary sequencer, a next generation sequencer, or the like after or without PCR amplification) of the nucleic acid subjected to the oxidation treatment is carried out, and the position of the 5-hydroxymethylcytosine is detected based on base substitution from C to T or from G to A by the sequencer.

Specifically, 5-hydroxymethylcytosine forms a complementary base pair with guanine, whereas oxidized 5-hydroxymethylcytosine forms a complementary base pair not with guanine but with adenine. Hence, the position of the 5-hydroxymethylcytosine can be specified by sequencing and comparing the nucleic acid sample before the oxidation and the oxidized nucleic acid sample.

More specifically, from a sequencing profile of a product obtained by the oxidation with the tungstic acid-based oxidizing agent, an optional desalination treatment, and the PCR amplification, the position of 5-hydroxymethylcytosine present in the nucleic acid can be clearly and efficiently distinguished from those of 5-methylcytosine and cytosine, and detected. This is because guanine, which is the complementary base of 5-methylcytosine and cytosine, is introduced into complementary sites of 5-methylcytosine and cytosine, whereas not only guanine, but also adenine is introduced into complementary sites of 5-hydroxymethylcytosine.

After the oxidation, the product optionally subjected to the desalination treatment is further treated preferably in an aqueous solution of 10 to 0.1% by mass of lithium bromide, lithium chloride, magnesium bromide, or the like (for example, a sodium phosphate, sodium acetate, or Tris hydrochloric acid buffer of pH 5 to 9) at 5 to 80° C. for 0.5 to 24 hours. Consequently, the ratio of adenine to the bases (guanine and adenine) introduced into the complementary sites of 5-hydroxymethylcytosine further increases to an extent that adenine is introduced almost exclusively. Hence, the position of 5-hydroxymethylcytosine present in the nucleic acid can be further clearly and efficiently distinguished from those of 5-methylcytosine and cytosine, and detected.

Example 1

In 50 ml of water, 1.25 μg of each of fluorescently labeled DNAs having the base sequences of SEQ ID NO: 1, respectively, was dissolved, and the pH was adjusted to 7.0 with a sodium phosphate-sodium chloride buffer solution. To such a solution, 165 μg of each of the oxidizing agents shown in Table 1 was added, and a reaction was allowed to proceed at 50° C. for 120 minutes.

A desalination treatment was conducted on the reaction mixture by using Micro BioSpin Column 6 Tris (Bio-Rad Laboratories, Inc.).

Subsequently, piperidine was added to the treated material at 10% by mass, and a heat treatment was conducted at 90° C. for 120 minutes.

The treated material was subjected to a freeze dry treatment, and the residue was analyzed by polyacrylamide gel electrophoresis.

SEQ ID NO: 1:
5'-Fluorescein-AAAAAAGXGAAAAAA-3' (X = hmC, mC, C).

Hereinafter, hmC represents 5-hydroxymethylcytosine, mC represents 5-methylcytosine, and C represents cytosine.

Figure 2:
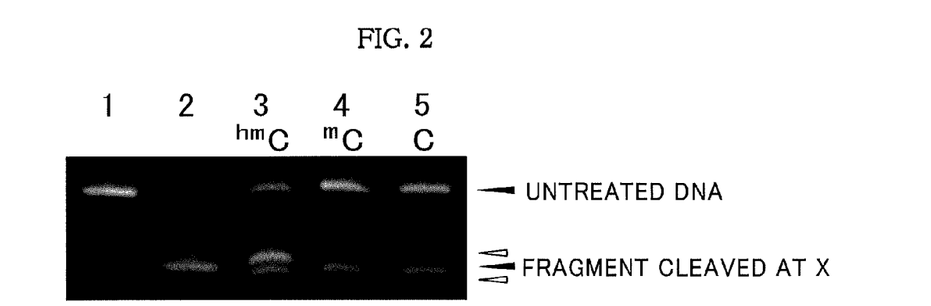
FIG. 2 is an image of polyacrylamide gel electrophoresis of products obtained from DNAs of SEQ ID NO: 1 by an oxidation treatment with $H_2WO_4/H_2O_2$ and a subsequent piperidine treatment.

FIG. 2 shows the results of polyacrylamide gel electrophoresis analysis of products obtained from the DNAs of SEQ ID NO: 1 by an oxidation treatment with $H_2WO_4/H_2O_2$ and a subsequent piperidine treatment.

Figure 3:
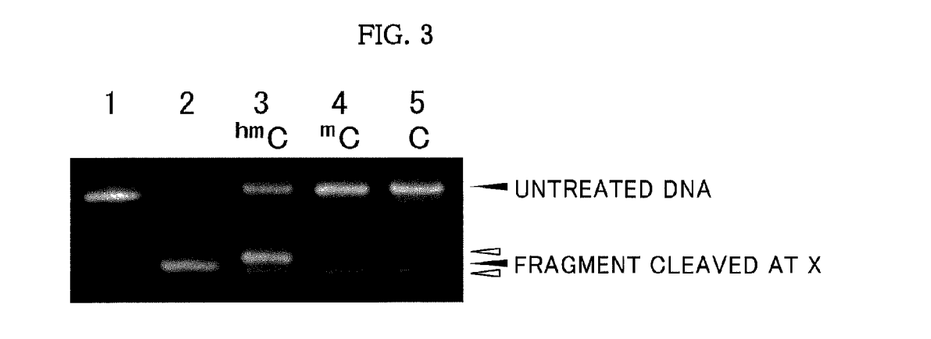
FIG. 3 is an image of polyacrylamide gel electrophoresis of products obtained from the DNAs of SEQ ID NO: 1 by an oxidation treatment with $K_2[\{W(=O)(O_2)_2(H_2O)\}_2(\mu\text{-}O)]$ and a subsequent piperidine treatment.

Meanwhile, FIG. 3 shows the results obtained by a similar treatment using $K_2[\{W(=O)(O_2)_2(H_2O)\}_2(\mu-O)]$ as the oxidizing agent.

Lane 1: A DNA before reaction;
Lane 2: A DNA having the same length (7 bases) as that of a DNA produced when a reaction of the oxidized 5-hydroxymethylcytosine occurs;
Lane 3: The DNA containing 5-hydroxymethylcytosine;
Lane 4: The DNA containing 5-methylcytosine; and
Lane 5: The DNA containing cytosine.

The hollow arrows represent slightly observed oxidation damage to guanine (oxidative decomposition of guanine base to 8-oxoguanine or imidazolone led to chain cleavage during the piperidine treatment).

In addition, Table 1 shows the ratio (%) of the fluorescence concentration of each treated fragment indicated by "Fragment cleaved at X" to the fluorescence concentration of "Untreated DNA" and "Fragment cleaved at X" shown in FIG. 2. Table 1 also shows the ratio (%) of the fluorescence concentration of a treated fragment to the fluorescence concentration of "Untreated DNA" and "Fragment cleaved at X," which were obtained from results of polyacrylamide gel electrophoresis analysis of each product obtained by the oxidation treatment with an oxidizing agent other than $H_2WO_4/H_2O_2$ and a piperidine treatment conducted in the same manner.

The results shown in FIGS. 2 and 3, and Table 1 indicates that the oxidizing agent of the present invention reacts with and oxidizes a DNA containing 5-hydroxymethylcytosine more specifically and selectively than the other oxidizing agents. This clearly indicates that the oxidizing agent of the present invention is excellent as a reagent for detecting 5-hydroxymethylcytosine in a nucleic acid.

TABLE 1

| Experimental Example | Oxidizing agent | hmC | mC | C |
|---|---|---|---|---|
| 1 | peroxo-W | 74.0 | 1.2 | 2.7 |
| 2 | $H_2WO_4 + H_2O_2$ | 66.7 | 4.0 | 6.2 |
| 3 | peroxo-Mo | 12.5 | 1.5 | 2.0 |
| 4 | $OsO_4$ | 12.3 | 3.6 | 0.5 |
| 5 | $MeReO_3 + H_2O_2$ | 3.1 | 1.2 | 2.4 | peroxo-W: $K_2[\{W(=O)(O_2)_2(H_2O)\}_2(\mu-O)]$
peroxo-Mo: $K_2[\{Mo(=O)(O_2)_2(H_2O)\}_2(\mu-O)]$ Example 2

DNAs (human TNF-β putative promoter region DNA fragments containing CpG, mCpG, and hmCpG, respectively) of SEQ ID NO: 2 were synthesized by the general purpose phosphoramidite method using a NTS H-6 DNA/RNA synthesizer. In 50 μl of water, 1.25 μg of each of the DNAs having a base sequence of SEQ ID NO: 2 was dissolved, and the pH was adjusted to 7.0 with a sodium phosphate-sodium chloride buffer solution. To such a solution, 165 μg of each of the oxidizing agents shown in Table 1 was added, and a reaction was allowed to proceed at 50° C. for 120 minutes.

The reaction mixture was subjected to a desalination treatment using Micro BioSpin Column 6 Tris (Bio-Rad Laboratories, Inc.), and a treated product I was obtained.

Subsequently, the treated product I was dissolved in 50 μl of water, and 435 μg of lithium bromide was added. Then, a reaction was allowed to proceed at 50° C. for 5 hours to obtain a treated product II.

The treated product II was subjected to a desalination treatment using Micro BioSpin Column 6 Tris (Bio-Rad Laboratories, Inc.).

Subsequently, a PCR primer having the base sequence of SEQ ID NO: 3 was added at 10% by mass to each of the treated products I and II, which were then sequenced by using BigDye (Registered Trademark) Terminator v3.1 Cycle Sequencing Kit (Applied Biosystems).

SEQ ID NO: 2:
5'-TGCCTGCCAC GCTGCCACTG CXGCTTCCTC TATAAAGGGA
CCTGAGCGTC CGGGCCCAGG GGCTCCGCAC AGCAGGTGAG
GCTCTCCTGC CCCATCTCCT-3' (X = hmC, mC, C).

SEQ ID NO: 3:
5'-GGAGATGGGG CAGGAG-3'

Figure 4:
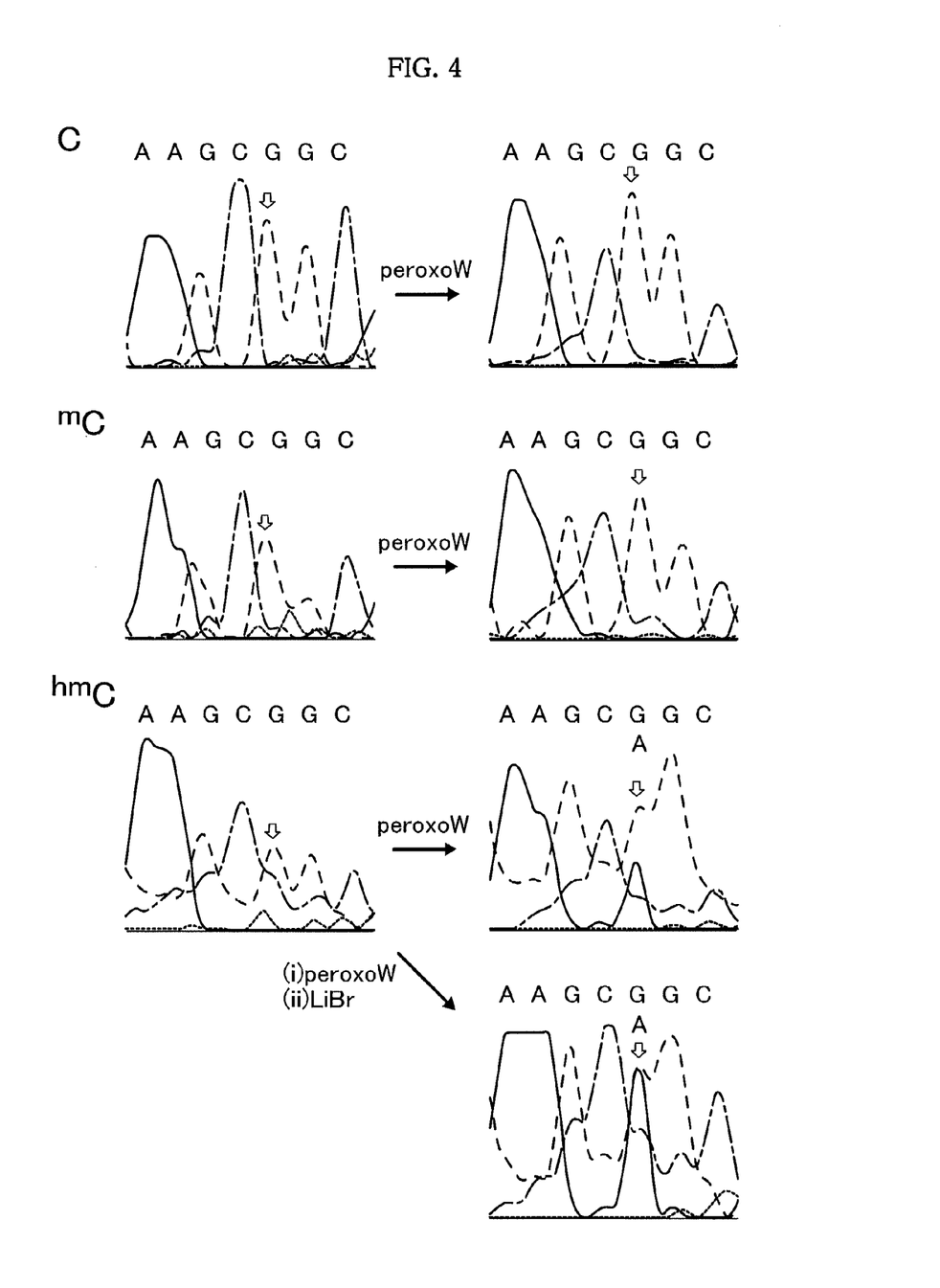
FIG. 4 shows diagrams showing sequencing profiles (right) of products obtained from DNAs of SEQ ID NO: 2 (human TNF-β putative promoter region DNA fragments containing CpG, mCpG, and hmCpG, respectively) by an oxidation treatment with $K_2[\{W(=O)(O_2)_2(H_2O)\}_2(\mu\text{-}O)]$ followed by deamination and PCR amplification, and profiles (left) before the treatments, where each solid line represents adenine, each dashed line represents guanine, each dashed-dotted line represents cytosine, and each dotted line represents thymine.

The results are shown in FIG. 4. FIG. 4 shows diagrams showing sequencing profiles (right) of products obtained from the DNAs of SEQ ID NO: 2 (the human TNF-β putative promoter region DNA fragments containing CpG, mCpG, and hmCpG, respectively) by an oxidation treatment with a tungstic acid-based oxidizing agent: $K_2[\{W(=O)(O_2)_2(H_2O)\}_2(\mu-O)]$ of the present invention followed by deamination and PCR amplification, and profiles (left) before the treatment, where each solid line represents adenine, each dashed line represents guanine, each dashed-dotted line represents cytosine, and each dotted line represents thymine.

From the sequencing profiles (the profiles on the right in FIG. 4) of the treated products I obtained by the oxidation with the tungstic acid-based oxidizing agent followed by the desalination treatment and the PCR amplification, it can be understood that guanine, which is a base complementary to 5-methylcytosine and cytosine, is introduced into complementary sites of 5-methylcytosine and cytosine, whereas not only guanine but also approximately 30 to 100% by mole of adenine is introduced into complementary sites of 5-hydroxymethylcytosine From a sequencing profile of a treated product II obtained by further treating the product, which was obtained by the oxidation and the desalination treatment, with lithium bromide followed by PCR amplification, it can be understood that only guanine, which is a complementary base of 5-methylcytosine and cytosine, is introduced into complementary sites of 5-methylcytosine and cytosine, whereas adenine is almost exclusively (50 to 100% by mole) introduced into complementary sites of 5-hydroxymethylcytosine.

Hence, by comparing a sequencing profile obtained by sequencing a product obtained by oxidation with a tungstic acid-based oxidizing agent optionally followed by a desalination treatment with a sequencing profile of a nucleic acid sample before the oxidation treatment, the position of 5-hydroxymethylcytosine present in a nucleic acid can be clearly distinguished from those of 5-methylcytosine and cytosine, and detected.

When a lithium bromide treatment is further carried out after the oxidation with a tungstic acid-based oxidizing agent and the optional desalination treatment, the ratio of adenine to the bases (guanine and adenine) introduced into complementary sites of 5-hydroxymethylcytosine is further increased. Hence, the position of 5-hydroxymethylcytosine present in a nucleic acid can be more clearly and efficiently detected from those of 5-methylcytosine and cytosine.

Example 3

Products were obtained by an oxidation treatment with $K_2[\{W(=O)(O_2)_2(H_2O)\}_2(\mu\text{-}O)]$ and a subsequent piperidine treatment in the same manner as in Example 1, except that DNAs having the following base sequences (A) to (K) of SEQ ID NOs: 4 to 14 and being fluorescently labeled with Fluorescein were used instead of the fluorescently labeled DNAs having the base sequences of SEQ ID NO: 1 used in Example 1. The products were analyzed by polyacrylamide gel electrophoresis.

```
SEQ ID NO: 4:
(A) Fluo-GATACTGXGT TGCAA

SEQ ID NO: 5:
(B) Fluo-AGTGCATXGC AAGAA

SEQ ID NO: 6:
(C) Fluo-GACATACXGA AGTGA

SEQ ID NO: 7:
(D) Fluo-AAGTGCAXGA TGCGA

SEQ ID NO: 8:
(E) Fluo-CACGTTTTTT AGTGATTTXG TCATTTTCAA

GTCGTCAAGT

SEQ ID NO: 9:
(F) Fluo-GAAAAACACA TACGTTGAAA ACXGGCATTG

TAGAACAGTG
```

```
-continued
SEQ ID NO: 10:
(G) Fluo-GTTGTGAGGX GCTGCCCCCA

SEQ ID NO: 11:
(H) Fluo-GCAGGGCCCA CTACXGCTTC CTCCAGATGA

SEQ ID NO: 12:
(I) Fluo-GAGTGAGXAG TAAGA

SEQ ID NO: 13:
(J) Fluo-AGAGCAGXTG ATGAA

SEQ ID NO: 14:
(K) Fluo-AAGCCAGXCG TATGA
```

Figure 5:
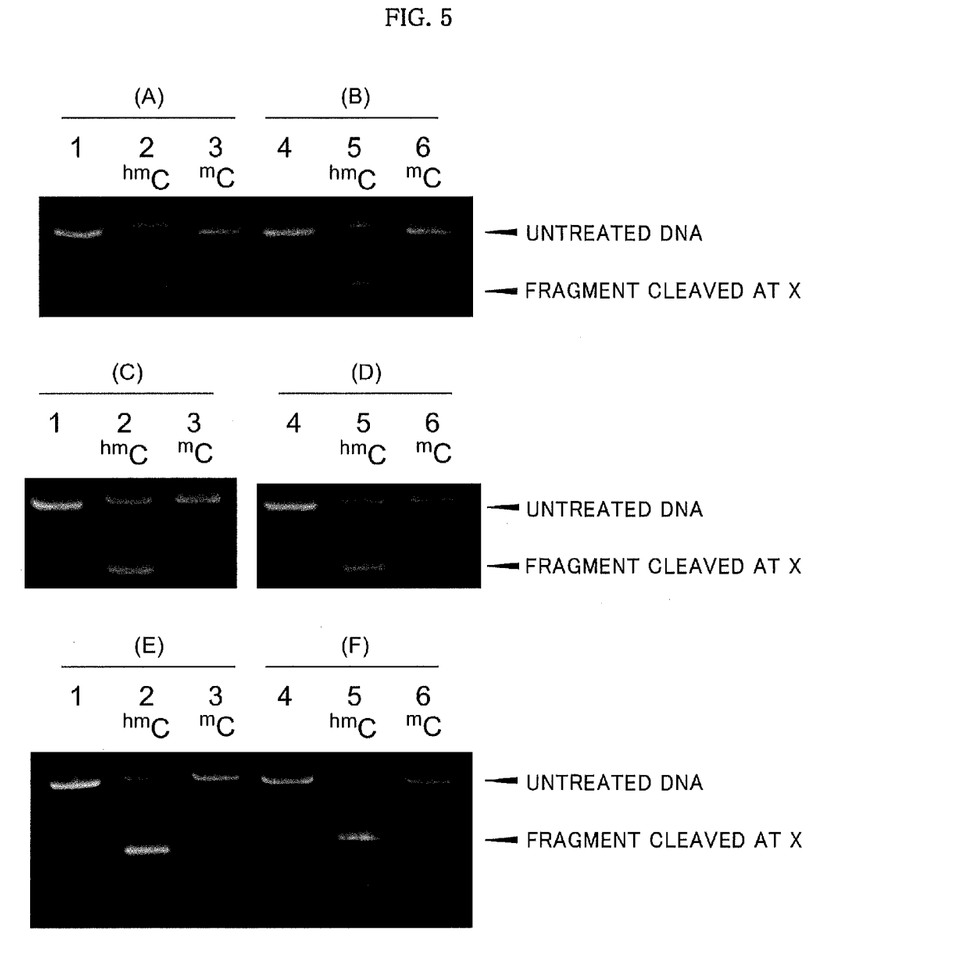
Figure 6:
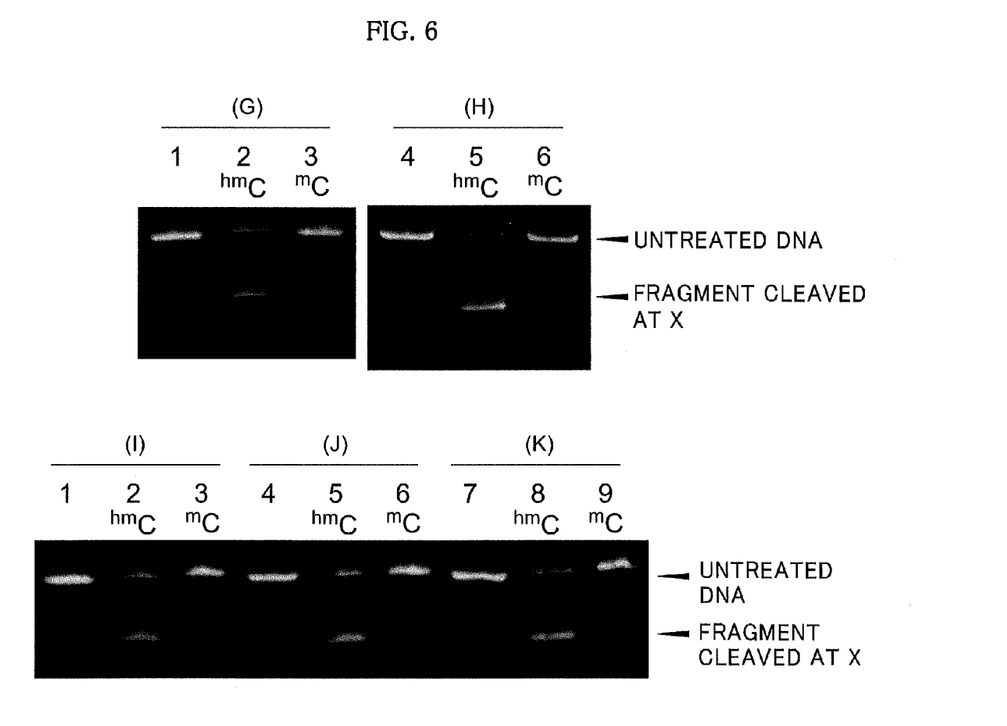

FIGS. 5 and 6 show the results. Parts (A) to (F) of FIG. 5 are polyacrylamide gel electrophoresis images showing the results of the cases where the DNAs of SEQ ID NO: 4 to 9 were used, and Parts (G) to (K) of FIG. 6 are polyacrylamide gel electrophoresis diagrams images showing the results of the cases where the DNA of SEQ ID NO: 10 to 14 were used.

In FIGS. 5 and 6, the lanes show the following samples.
Lanes 1, 4, and 7: DNAs containing cytosine;
Lanes 2, 5, and 8: DNAs containing 5-hydroxymethylcytosine;
Lanes 3, 6, and 9: DNAs containing 5-methylcytosine.

The results shown in FIGS. 5 and 6 clearly demonstrate that the method of the present invention makes it possible to distinguish and selectively detect hmC from mC, because only DNAs containing 5-hydroxymethylcytosine (hmC) are detected, and DNAs containing 5-methylcytosine (mC) are not detected.

INDUSTRIAL APPLICABILITY

The present invention makes it possible to chemically, easily, and accurately detect the presence and the position of 5-hydroxymethylcytosine in a nucleic acid. Hence, the present invention is extremely useful as a core technology for investigating the reprogramming of a gene function in all the fields associated with epigenetics technologies, such as the fields of cancer, aging, and regenerative medicine.

The invention claimed is:

1. A method for detecting 5-hydroxymethylcytosine in a nucleic acid, comprising the steps of:
   (1) oxidizing 5-hydroxymethylcytosine possibly present in a nucleic acid sample by treating the nucleic acid sample with a tungstic acid-based oxidizing agent; and
   (2) determining the position of the oxidized 5-hydroxymethylcytosine in the nucleic acid sample.

2. The method according to claim 1, wherein
   the tungstic acid-based oxidizing agent is at least one selected from the group consisting of
   (1) peroxotungstic acid, or a salt thereof,
   (2) tungstic acid, or a salt thereof, and
   (3) combinations of peroxotungstic acid, tungstic acid, or a salt thereof with a reoxidizing agent.

3. The method according to claim 1, wherein
   the tungstic acid-based oxidizing agent is at least one selected from the group consisting of $K_2[\{W(=O)(O_2)_2(H_2O)\}_2(\mu\text{-}O)]$, $H_2WO_4/H_2O_2$, and $K_2WO_4/H_2O_2$.

4. The method according to claim 1, wherein
   the step (2) comprises a step of determining the position of the oxidized 5-hydroxymethylcytosine by cleaving the oxidized nucleic acid sample at the position of the oxidized 5-hydroxymethylcytosine by a deamination treatment, and measuring the size of a fragment of the nucleic acid.

5. The method according to claim 1, wherein
   the step (2) comprises a step of determining the position of the oxidized 5-hydroxymethylcytosine by sequencing the oxidized nucleic acid sample.

6. The method according to claim 1, wherein
   the nucleic acid is a DNA.

7. A kit for detecting 5-hydroxymethylcytosine in a nucleic acid, comprising at least one tungstic acid-based oxidizing agent selected from the group consisting of
   (1) peroxotungstic acid, or a salt thereof,
   (2) tungstic acid, or a salt thereof, and
   (3) combinations of peroxotungstic acid, tungstic acid, or a salt thereof with a reoxidizing agent.

8. The kit according to claim 7, further comprising at least one selected from the group consisting of reagents for a deamination treatment of an oxidized nucleic acid sample, and pH buffer solutions.

* * * * *

SEQUENCE LISTING

```
<160> NUMBER OF SEQ ID NOS: 14

<210> SEQ ID NO 1
<211> LENGTH: 15
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (8)..(8)
<223> OTHER INFORMATION: n stands for 5-hydroxymethylcytosine,
      5-methylcytosine, or cytosine.

<400> SEQUENCE: 1
aaaaaagnga aaaaa                                                       15

<210> SEQ ID NO 2
<211> LENGTH: 100
<212> TYPE: DNA
<213> ORGANISM: Artificial
<220> FEATURE:
<223> OTHER INFORMATION: sample
```

```
<220> FEATURE:
<221> NAME/KEY: misc_feature
<222> LOCATION: (22)..(22)
<223> OTHER INFORMATION: n stands for 5-hydroxymethylcytosine,
      5-methylcytosine or cytosine.

<400> SEQUENCE: 2
tgcctgccac gctgccactg cngcttcctc tataaaggga cctgagcgtc cgggcccagg    60
ggctccgcac agcaggtgag gctctcctgc cccatctcct                         100

<210> SEQ ID NO 3
<211> LENGTH: 16
<212> TYPE: DNA
<213> ORGANISM: Artificial
<220> FEATURE:
<223> OTHER INFORMATION: primer

<400> SEQUENCE: 3
ggagatgggg caggag                                                    16

<210> SEQ ID NO 4
<211> LENGTH: 15
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (8)..(8)
<223> OTHER INFORMATION: n stands for 5-hydroxymethylcytosine,
      5-methylcytosine, or cytosine.

<400> SEQUENCE: 4
gatactgngt tgcaa                                                     15

<210> SEQ ID NO 5
<211> LENGTH: 15
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (8)..(8)
<223> OTHER INFORMATION: n stands for 5-hydroxymethylcytosine,
      5-methylcytosine, or cytosine.

<400> SEQUENCE: 5
agtgcatngc aagaa                                                     15

<210> SEQ ID NO 6
<211> LENGTH: 15
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
```

```
<222> LOCATION: (8)..(8)
<223> OTHER INFORMATION: n stands for 5-hydroxymethylcytosine,
      5-methylcytosine, or cytosine.

<400> SEQUENCE: 6
gacatacnga agtga                                                     15

<210> SEQ ID NO 7
<211> LENGTH: 15
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (8)..(8)
<223> OTHER INFORMATION: n stands for 5-hydroxymethylcytosine,
      5-methylcytosine, or cytosine.

<400> SEQUENCE: 7
aagtgcanga tgcga                                                     15

<210> SEQ ID NO 8
<211> LENGTH: 40
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (19)..(19)
<223> OTHER INFORMATION: n stands for 5-hydroxymethylcytosine,
      5-methylcytosine, or cytosine.

<400> SEQUENCE: 8 cacgttttttt agtgatttng tcattttcaa gtcgtcaagt                         40

<210> SEQ ID NO 9
<211> LENGTH: 40
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (23)..(23)
<223> OTHER INFORMATION: n stands for 5-hydroxymethylcytosine,
      5-methylcytosine, or cytosine.

<400> SEQUENCE: 9
gaaaaacaca tacgttgaaa acnggcattg tagaacagtg                          40

<210> SEQ ID NO 10
<211> LENGTH: 20
<212> TYPE: DNA
<213> ORGANISM: Artificial
<220> FEATURE:
<223> OTHER INFORMATION: sample
<220> FEATURE:
```

```
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (10)..(10)
<223> OTHER INFORMATION: n stands for 5-hydroxymethylcytosine,
      5-methylcytosine, or cytosine.

<400> SEQUENCE: 10
gttgtgaggn gctgccccca                                              20

<210> SEQ ID NO 11
<211> LENGTH: 30
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (15)..(15)
<223> OTHER INFORMATION: n stands for 5-hydroxymethylcytosine,
      5-methylcytosine, or cytosine.

<400> SEQUENCE: 11
gcagggccca ctacngcttc ctccagatga                                   30

<210> SEQ ID NO 12
<211> LENGTH: 15
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (8)..(8)
<223> OTHER INFORMATION: n stands for 5-hydroxymethylcytosine,
      5-methylcytosine, or cytosine.

<400> SEQUENCE: 12
gagtgagnag taaga                                                   15

<210> SEQ ID NO 13
<211> LENGTH: 15
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (8)..(8)
<223> OTHER INFORMATION: n stands for 5-hydroxymethylcytosine,
      5-methylcytosine, or cytosine.

<400> SEQUENCE: 13
agagcagntg atgaa                                                   15

<210> SEQ ID NO 14
<211> LENGTH: 15
```

```
<212> TYPE: DNA
<213> ORGANISM: Artificial
<220> FEATURE:
<223> OTHER INFORMATION: sample
<220> FEATURE:
<221> NAME/KEY: modified_base
<222> LOCATION: (1)..(1)
<223> OTHER INFORMATION: fluorescein-labeled
<220> FEATURE:
<221> NAME/KEY: misc_feature
<222> LOCATION: (8)..(8)
<223> OTHER INFORMATION: n stands for 5-hydroxymethylcytosine,
      5-methylcytosine, or cytosine.

<400> SEQUENCE: 14
aagccagncg tatga                                                   15
```